United States Patent
Naraschkewitz et al.

(10) Patent No.: US 7,601,682 B2
(45) Date of Patent: Oct. 13, 2009

(54) MIXTURES OF 3-(4-METHYLCYCLOHEX-3-ENYL)BUTYRALDEHYDE AND AMBROCENIDE® AND CORRESPONDING USES AND METHODS

(75) Inventors: Fred Naraschkewitz, Buchholz Nordheide (DE); Marcus Eh, Holzminden (DE)

(73) Assignee: SYMRISE GmbH & Co. KG, Holzminden (DE)

( * ) Notice: Subject to any disclaimer, the term of this patent is extended or adjusted under 35 U.S.C. 154(b) by 31 days.

(21) Appl. No.: 11/967,652

(22) Filed: Dec. 31, 2007

(65) Prior Publication Data

US 2008/0161224 A1  Jul. 3, 2008

(30) Foreign Application Priority Data

Jan. 2, 2007   (EP) ................... 07100015

(51) Int. Cl.
*A61K 8/00* (2006.01)
*C07D 317/70* (2006.01)
*C07D 47/02* (2006.01)
*A61Q 5/00* (2006.01)
*A61Q 13/00* (2006.01)
*A61Q 90/00* (2009.01)

(52) U.S. Cl. ................. 512/1; 512/18; 512/25; 549/432; 568/448

(58) Field of Classification Search ............ 512/1, 512/12, 18; 549/432; 568/374, 448
See application file for complete search history.

(56) References Cited

U.S. PATENT DOCUMENTS

| 2,584,539 A | 2/1952 | Bordenca et al. |
| 2,710,825 A | 6/1955 | Lazier et al. |
| 4,334,100 A | 6/1982 | Hagen et al. |
| 5,892,062 A | 4/1999 | Pickenhagen et al. |

FOREIGN PATENT DOCUMENTS

| EP | 0 011 272 A3 | 5/1980 |
| EP | 0 857 723 A1 | 8/1998 |
| EP | 1 201 738 A1 | 5/2002 |

OTHER PUBLICATIONS

Supplementary European Search Report for Application No. EP 07 12 1171 dated Apr. 9, 2008.

*Primary Examiner*—James Seidleck
*Assistant Examiner*—Aaron Greso
(74) *Attorney, Agent, or Firm*—Connolly Bove Lodge & Hutz LLP

(57) ABSTRACT

Mixtures are described which comprise or consist of 3-(4-methylcyclohex-3-enyl)butyraldehyde (limonenal) and (4aR,5R,7aS,9R)-octahydro-2,2,5,8,8,9a-hexamethyl-4H-4a,9-methanoazuleno(5,6-d)-1,3-dioxole (Ambrocenide®), the weight ratio of limonenal to Ambrocenide® being in the range from 150:1 to 2500:1.

13 Claims, No Drawings

MIXTURES OF 3-(4-METHYLCYCLOHEX-3-ENYL)BUTYRALDEHYDE AND AMBROCENIDE® AND CORRESPONDING USES AND METHODS

RELATED APPLICATIONS

This application claims benefit of European application 07 100 015.2 filed Jan. 2, 2007.

According to a first feature, the present invention relates to mixtures comprising or consisting of 3-(4-methylcyclohex-3-enyl)butyraldehyde (limonenal) and (4aR,5R,7aS,9R)-octahydro-2,2,5,8,8,9a-hexamethyl-4H-4a,9-methanoazuleno (5,6-d)-1,3-dioxole) (CAS no. 211299-54-6; hereafter: Ambrocenide). A further feature relates to the use of Ambrocenide® for masking an unwanted olfactory note of limonenal, and to corresponding methods of masking said olfactory note of limonenal. Finally, the invention further relates to the use of a mixture according to the invention as a fragrance with a fresh, citrus-like note.

Ambrocenide® has the following structure (cf. also EP 0 857 723):

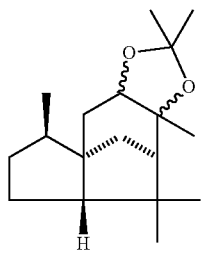

The wavy lines here can denote, independently of one another, the alpha or beta configuration. Ambrocenide® can comprise one, two, three or all of the following diastereoisomers:

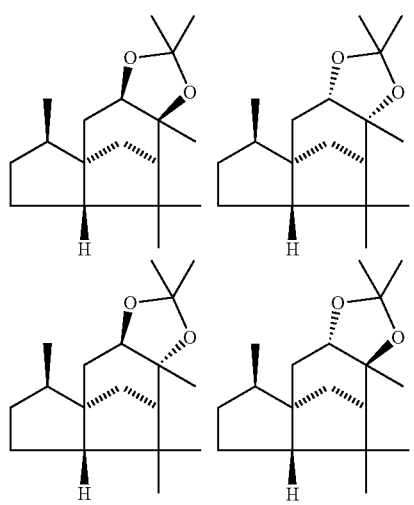

3-(4-Methylcyclohex-3-enyl)butyraldehyde (limonenal) is already known from the state of the art:

U.S. Pat. No. 2,584,539 describes the hydroformylation reaction of limonene to 3-(4-methylcyclohex-3-enyl)butyraldehyde. The odour of 3-(4-methylcyclohex-3-enyl)butyraldehyde is described as pleasant and long-lasting; limonenal is said to be used in a mixture with or as a substitute for hydroxycitronellal in perfume mixtures. It should be noted in this regard that hydroxycitronellal has a flowery odour.

U.S. Pat. No. 2,710,825 describes the preparation of 3-(4-methylcyclohex-3-enyl)butyraldehyde, inter alia, from limonene. The odour of 3-(4-methylcyclohex-3-enyl)butyraldehyde is described as stronger and longer-lasting than that of citral and it is maintained that the butyraldehyde (limonenal) additionally imparts a green or fresh note.

EP 011 272 A3 describes the preparation of aldehydes by the hydroformylation of olefins. Inter alia, the preparation of 3-(4-methylcyclohex-3-enyl)butyraldehyde by the hydroformylation of limonene is described. The odour of 3-(4-methylcyclohex-3-enyl)butyraldehyde is reported to be an agrumen and rhubarb note. It is also mentioned that this compound can be used not only in fine perfumery but also e.g. for the perfuming of soaps, cleaning products and detergents or fabric softeners.

In our own experiments 3-(4-methylcyclohex-3-enyl)butyraldehyde (limonenal) was found to have a very intense, modern, fresh, green, aldehydic, somewhat fatty and citrus-like odour coupled with flowery-fruity notes. The green citrus-like odour is reminiscent of the peel of citrus fruits, especially lemons and limes. However, the fatty olfactory note is increasingly perceived as troublesome because it restricts the ability of limonenal to be used in fragrance mixtures (especially perfume compositions).

EP 0 857 723 describes the preparation and use of cyclic cedrene acetals, including Ambrocenide®. In general, the compounds described in said patent possess olfactory properties of the ambergris type and simultaneously create a strong, radiant effect which intensifies very different perfume notes and prolongs their olfactory action. However, a mixture of 3-(4-methylcyclohex-3-enyl)butyraldehyde (limonenal) and Ambrocenide® is not disclosed.

References to an odour-enhancing action of Ambrocenide® have not been published hitherto.

The primary object of the present invention was to provide a substance (mixture or single compound) that partially or completely masks the fatty olfactory notes of limonenal.

In particular, the object of the present invention was to provide a substance (mixture or single compound) whose olfactory characteristic is very similar to that of limonenal, but only comprises the fatty olfactory notes of limonenal to a reduced extent, if at all.

Preferably, said object should be achieved by the provision of a means of masking the fatty olfactory note of limonenal.

According to a first feature, said object is achieved according to the invention by a mixture comprising or consisting of 3-(4-methylcyclohex-3-enyl)butyraldehyde (limonenal) and 4aR,5R,7aS, 9R)-octahydro-2,2,5,8,9a-hexamethyl-4H-4a,9-methanoazuleno(5,6-d)-1,3-dioxole (Ambrocenide), the weight ratio of limonenal to Ambrocenide being in the range from 150:1 to 2500:1.

Surprisingly, mixtures according to the invention have an odour which, despite the large proportion by weight of limonenal, now only comprises barely perceptible fatty olfactory notes, if any. Surprisingly, Ambrocenide® is able to mask the fatty olfactory note of limonenal without having a troublesome influence in the mixtures according to the invention with olfactory notes of the ambergris type. The decisive factor here for success in perfume formulations (masking without incorporation of dominant ambergris notes) is the chosen weight ratio of limonenal to Ambrocenide®, which should be in the range from 600:1 to 2500:1. Particularly preferred weight ratios of limonenal to Ambrocenide are in the range from 800:1 to 2500:1. In this connection, see also the detailed explanations below.

The compounds limonenal and Ambrocenide® contained in mixtures according to the invention can each be present as pure enantiomers or as mixtures of enantiomers. As already explained above, Ambrocenide® can be in the form of one, two, three or all of the diastereoisomers shown above.

In the preparation of the mixtures according to the invention, especially in order to simplify handling and dosing, Ambrocenide® is preferably used in a mixture with diluents or solvents. Preferred solutions of Ambrocenide® are 1-50 wt. %, particularly 5 to 25 wt. %, preferably in solvents acceptable in perfumery. Preferred solvents acceptable in perfumery are ethanol, dipropylene glycol (DPG), propylene glycol, 1,2-butylene glycol, glycerol, diethylene glycol-monoethyl ether, diethyl phthalate (DEP), isopropyl myristate (IPM), triethyl citrate (TEC), benzyl benzoate (BB) and benzyl acetate.

A mixture according to the invention accordingly preferably comprises one or more diluents or solvents selected from the group consisting of ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), benzyl benzoate (BB) and benzyl acetate, particular preference being afforded to ethanol, diethyl phthalate, propylene glycol, dipropylene glycol, triethyl citrate, benzyl benzoate and isopropyl myristate.

Of particular value for industrial perfumery are mixtures according to the invention in which the weight ratio of Ambrocenide® to the total amount of said diluent(s) or solvent(s) is in the range from 1:99 to 1:1, preferably in the range from 5:95 to 1:3. The preferred weight ratios apply especially when no other fragrances, or only a small number and/or amount of other fragrances, are present apart from limonenal and Ambrocenide®. As soon as the number and amount of other fragrances is appreciable, it may be advantageous in specific cases to increase the total amount of diluent(s) or solvent(s) beyond the amounts (ratios) indicated as preferred.

In our own experiments mixtures of limonenal and Ambrocenide® in the above-mentioned (preferred) proportions according to the invention were found to have an odour which corresponded extensively to that of pure limonenal, except that the unwanted fatty notes of limonenal were largely or even completely suppressed (masked). Due to suppression of the fatty olfactory notes, the odour of the mixture according to the invention seems markedly natural and particularly complex in olfactory terms.

Ambrocenide® was used in our own experiments as a 10% solution in DPG.

Details are given in the Table below:

| Proportions by weight | | Olfactory notes (0 = imperceptible to 6 = very strongly perceptible) | | | | | |
|---|---|---|---|---|---|---|---|
| Limonenal | Ambrocenide ® | fresh | citrus | green | fatty | wood | ambergris |
| 100 | — | 4 | 6 | 3 | 4 | 0 | 0 |
| 3500 | 1 | 4 | 6 | 3 | 4 | 0 | 1 |
| 1990 | 1 | 4 | 6 | 3 | 1 | 0 | 1 |
| 990 | 1 | 4 | 6 | 3 | 0 | 1 | 1 |
| 190 | 1 | 2 | 3 | 1 | 0 | 5 | 4 |
| 90 | 1 | 1 | 2 | 0 | 0 | 6 | 5 |
| — | 100 | 0 | 0 | 0 | 0 | 6 | 5 |

It is recognized that, especially with weight ratios of limonenal to Ambrocenide® of 990:1 and 1990:1, complete or at least almost complete suppression of the fatty aldehydic note of limonenal is achieved. Moreover, with weight ratios of 990:1 and 1990:1, only very weak ambergris notes were perceived. The sensory assessment of the mixtures with weight ratios of 990:1 and 1990:1 was overall the most advantageous.

Preferably, a mixture according to the invention comprises none of the 3-(4-methylcyclohexyl)butyraldehyde usually formed as a by-product in the preparation of limonenal from limonene.

A mixture according to the invention is preferably a fragrance mixture (e.g. perfume composition) which, apart from limonenal and Ambrocenide®, comprises at least an equal proportion by weight of one or more other fragrances. In particular, such a fragrance mixture can be a perfume composition (a perfume oil).

Mixtures according to the invention, and especially perfume compositions according to the invention, can be incorporated into a number of products or applied to such products. The invention therefore further relates to products comprising a mixture according to the invention.

Mixtures according to the invention are particularly suitable for use in products containing surfactants. In other words, there is a frequent demand especially for the perfuming of formulations containing surfactants, e.g. cleaning products (especially dishwashing detergents and all-purpose cleaners)—for fragrance mixtures with a citrus top note and pronounced naturalness, fatty notes being undesirable.

In mixtures according to the invention, Ambrocenide® is also observed to have a fixing action on limonenal. Compared with pure limonenal, a mixture according to the invention is capable of achieving not only a citrus top note with pronounced naturalness, without a troublesome fatty note, but also a greater lingering power at the same time. Fixatives (like Ambrocenide above) increase the lingering power of fragrances (like limonenal above), whether it be by lowering their vapour pressure or by intensifying the odour of the (other) fragrances (e.g. lowering the threshold value).

The mixtures according to the invention are particularly suitable for use in products containing surfactants.

The product (preferably containing surfactants) is preferably one of the following:

an acidic, alkaline or neutral cleaning product, preferably selected from the group comprising all-purpose cleaners, floor cleaners, window cleaners, dishwashing detergent, bath and sanitaryware cleaners, scouring cream, solid and liquid WC cleaners, carpet cleaning powders and foams, liquid detergents, powder detergents, fabric preconditioners like bleach, soaker and stain removers, fabric softeners, washing soaps, washing tablets, disinfectants and surface disinfectants;

an air purifier in liquid form, in gel form, applied to a solid carrier or in the form of an aerosol spray;

a wax or a polish, preferably selected from the group comprising furniture polishes, floor waxes and shoe polishes; or a body care product, preferably selected from the group comprising solid and liquid soaps, shower gels, shampoos, shaving soaps, shaving foams, bath oils, cosmetic emulsions of the oil-in-water, water-in-oil and water-in-oil-in-water type, e.g. skin creams and lotions, face creams and lotions, sun creams and lotions, after-sun creams and lotions, hand creams and lotions, foot creams and lotions, depilatory creams and lotions, after-shave creams and lotions and tanning creams and lotions, hair care products, e.g. hair sprays, hair gels, hair lotions, hair rinses, permanent and semipermanent hair dyes, hair styling products like cold waving and straightening products, hair tonics, and hair creams and lotions, deodorants and antiperspirants, e.g. armpit sprays, roll-ons, deodorant sticks and deodorant creams, and decorative cosmetic products.

Ingredients with which the mixtures according to the invention can be combined are e.g.: preservatives, abrasives, anti-acne agents, agents for combating skin ageing, antibacterial agents, anticellulite agents, antidandruff agents, anti-inflammatories, agents for preventing irritation, agents for inhibiting irritation, antimicrobial agents, antioxidants, astringents, perspiration inhibiting agents, antiseptics, antistatics, binders, buffers, carriers, chelating agents, cell stimulants, cleansing agents, nurturing agents, depilatories, surface-active substances, deodorants, antiperspirants, softeners, emulsifiers, enzymes, ethereal oils, fibres, film-forming agents, fixatives, foaming agents, foam stabilizers, antifoams, foam boosters, fungicides, gelling agents, jellying agents, hair care agents, hair styling agents, hair straightening agents, moisturizing agents, moistening substances, humectants, bleaching agents, starching agents, stain-removing agents, optical brighteners, impregnating agents, dirt repellents, friction-reducing agents, lubricants, moisturizing creams, ointments, opacifiers, plasticizers, hiding agents, polish, lustring agents, polymers, powders, proteins, superfatting agents, gently scouring agents, silicones, skin soothing agents, skin cleansers, skin nurturing agents, skin healing agents, skin lightening agents, skin protecting agents, skin softening agents, cooling agents, skin cooling agents, warming agents, skin warming agents, stabilizers, UV absorbers, UV filters, detergents, fabric softeners, suspending agents, skin tanning agents, thickeners, vitamins, oils, waxes, fats, phospholipids, saturated fatty acids, monounsaturated or polyunsaturated fatty acids, α-hydroxy acids, polyhydroxy fatty acids, liquefying agents, colourants, colour protecting agents, pigments, anticorrosives, flavourings, taste providing agents, fragrances, polyols, surfactants, electrolytes, organic solvents or silicone derivatives.

The present invention further relates to the use of Ambrocenide® for masking the fatty olfactory note of limonenal.

A corresponding method according to the invention for masking the fatty olfactory note of limonenal comprises the following step:

mixing of limonenal with an amount of Ambrocenide® that partially or completely masks the fatty olfactory note of limonenal.

It is understood that the amount of Ambrocenide® used in a method according to the invention is preferably chosen so that the woody and/or ambergris note of the Ambrocenide® does not dominate over the fresh and/or citrus note of the limonenal.

Particularly good masking results are achieved if the weight ratio of limonenal to Ambrocenide® in the resulting mixture is adjusted to a value in the range from 600:1 to 2500:1, preferably in the range from 800:1 to 2500:1. Adjusting the weight ratios to the preferred values ensures that the woody and/or ambergris note of the Ambrocenide® does not dominate over the fresh and/or citrus notes of the limonenal.

Preferred mixtures according to the invention are preferably prepared by the methods according to the invention.

A mixture according to the invention, or a mixture prepared by a method according to the invention, can be used with outstanding results as a fragrance with a fresh, citrus-like note because the fatty olfactory note obtained when using pure limonenal does not occur to a troublesome extent when using said mixture.

A mixture according to the invention can be used as a fragrance mixture for producing an intense, natural citrus odour, especially when the weight ratio of limonenal to Ambrocenide® is in the range from 600:1 to 2500:1.

A corresponding method according to the invention for providing (a) hair or (b) textile fibres with the complex olfactory impression of a natural citrus odour comprises the following steps:

preparation of a mixture according to the invention, and
application of the mixture to the hair or the textile fibres.

One particularly suitable mixture for the uses according to the invention or the corresponding methods is a solution comprising:

(a) water,
(b) Ambrocenide® and limonenal in the (preferred) weight ratios given above, and
(c) one or more surfactants, the concentration of limonenal in the solution being in the range from $10^{-7}$ to $10^{-1}$ wt. %. Other fragrances and/or miscellaneous conventional additives may be present.

Examples of fragrances with which a mixture according to the invention can advantageously be combined can be found e.g. in S. Arctander, Perfume and Flavor Materials, vol. I and II, Montclair, N.J., 1969, Selbstverlag, or K. Bauer, D. Garbe and H. Surburg, Common Fragrance and Flavor Materials, 4th ed., Wiley-VCH, Weinheim 2001.

Apart from limonenal and Ambrocenide® (in the indicated proportions), preferred perfume compositions (perfume oils) according to the invention comprise at least an equal proportion by weight of one or more other fragrances. Preferred mixtures (especially perfume compositions) according to the invention thus preferably comprise, apart from limonenal and Ambrocenide®, an equal or higher proportion by weight of one or more other fragrances.

Apart from limonenal and Ambrocenide®, perfume compositions according to the invention preferably comprise one, two, three, four, five, six, seven, eight, nine, ten or more other fragrances.

Perfume compositions according to the invention which comprise limonenal and Ambrocenide® in the weight ratios according to the invention can be used in concentrated form, in solutions or in the modified forms described below for the perfuming of e.g. acidic, alkaline and neutral cleaning products such as carpet cleaning powders and foams, liquid detergents, powder detergents, fabric preconditioners like bleach, soaker and stain remover, fabric softeners, washing soaps, washing tablets, body care products such as solid and liquid soaps, shower gels, shampoos, cosmetic emulsions of the oil-in-water, water-in-oil and water-in-oil-in-water type, and hair care products such as hairsprays, hair gels, strengthening hair lotions, hair rinses, permanent and semipermanent hair dyes, hair styling products like cold waving and straightening products, hair tonics, and hair creams and lotions.

Perfume compositions according to the invention which comprise limonenal and Ambrocenide® in the weight ratios according to the invention can be used in perfume formulations in liquid form, either undiluted or diluted with a solvent. Examples of suitable solvents for this purpose are ethanol, isopropanol, diethylene glycol monoethyl ether, glycerol, propylene glycol, 1,2-butylene glycol, dipropylene glycol, diethyl phthalate, triethyl citrate, isopropyl myristate, etc.

Mixtures according to the invention, and especially perfume compositions according to the invention, can be adsorbed on a carrier to ensure both a fine distribution of the fragrances in the product and a controlled release when applied. Such carriers can be porous inorganic materials such as light sulfate, silica gels, zeolites, gypsums, clays, clay granules, gas concrete, etc., or organic materials such as woods and cellulose-based substances.

Mixtures according to the invention, and especially perfume compositions according to the invention, can also be microencapsulated or spray-dried or in the form of inclusion complexes or extrusion products, and can be added in this form to the product to be perfumed.

Optionally, the properties of mixtures according to the invention modified in this way, especially perfume compositions (perfume oils) according to the invention modified in this way, can be further optimized, in respect of a more specific perfume release, by coating with suitable materials; waxy plastics, e.g. polyvinyl alcohol, are preferably used for this purpose.

Microencapsulation of mixtures according to the invention, especially perfume compositions according to the invention, can be effected e.g. by the so-called coacervation process with the aid of capsule materials made e.g. of polyurethane-like substances or soft gelatin. Spray-dried perfume oils can be prepared e.g. by spray drying an emulsion or dispersion containing the perfume oil, it being possible for modified starches, proteins, dextrins and vegetable gums to be used as carriers. Inclusion complexes can be prepared e.g. by introducing dispersions of the perfume oil and cyclodextrins or urea derivatives into a suitable solvent, e.g. water. Extrusion products can be prepared by melting the perfume oils with a suitable waxy substance and by extrusion with subsequent solidification, optionally in a suitable solvent, e.g. isopropanol.

Preferred products which can be used within the framework of the present invention are (a) perfume oils for formulations containing surfactants, e.g. cleaning products, detergents, fabric softeners and body care products, and (b) the corresponding formulations themselves which contain surfactants.

The surfactant-containing formulations which can be used within the framework of the present invention generally include substances from the class of anionic surfactants, e.g. carboxylates, sulfates, sulfonates and phosphates, cationic surfactants, e.g. quaternary ammonium salts, amphoteric surfactants, e.g. betaines, and non-ionic surfactants, e.g. ethoxylates and propoxylates.

Preferred anionic surfactants are sulfates and sulfonates. Preferred sulfates are those having 12 to 18 carbon atoms and a degree of ethoxylation of 1 to at most 5. Sodium laurylethersulfate, preferably having a mean degree of ethoxylation of 2 to 4, is particularly preferred.

Particularly preferred sulfonates are linear sodium alkylbenzenesulfonates having an average of approx. 12 carbon atoms in the alkyl chain, said alkyl chains consisting of homologous radicals having 10 to 14 carbon atoms ("dodecylbenzenesulfonate").

Preferred compounds from the group of non-ionic surfactants are ethoxylated fatty alcohols obtained by the ethoxylation of alcohols having 12 to 18 carbon atoms (fatty alcohol ethoxylates having 12 to 18 C atoms). The degree of ethoxylation here can vary within wide limits, but particularly preferred products are those having an average degree of ethoxylation of 5 to 10 or, in particular, 7 mol of added ethylene oxide per mol of fatty alcohol.

Particularly preferred betaines are those of the acid amide type having the structure shown:

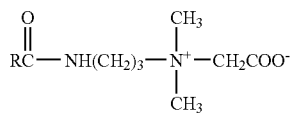

A preferred radical RC=O is the coconut oil fatty acid cut in which lauric acid is the main constituent at 45-50%.

In combination with selected surfactants, the favourable properties of the mixtures according to the invention, especially the perfume compositions (perfume oils) according to the invention, are particularly pronounced. A corresponding surfactant-containing product according to the invention preferably comprises, apart from limonenal and Ambrocenide® (in the weight ratios according to the invention), one or more surfactants selected from the group comprising:

linear alkylbenzenesulfonates (especially those mentioned above, e.g. linear sodium alkylbenzenesulfonates), fatty alcohol ethoxylates having 12-18 C atoms (especially those mentioned above, e.g. those having the degree of ethoxylation identified above as preferred), laurylethersulfates (especially those mentioned above, e.g. the sodium laurylethersulfate mentioned above) and betaines (especially those mentioned above, e.g. betaines of the acid amide type having the structure shown above).

Linear alkylbenzenesulfonates and fatty alcohol ethoxylates having 12-18 C atoms are preferably used together with one another here, especially in heavy-duty detergent powders.

Likewise, laurylethersulfates (especially the sodium laurylethersulfate mentioned above) and betaines (especially those of the acid amide type having the structure shown above) are preferably used together with one another, especially in light-duty detergents, shampoos and shower gels.

The concentration of surface-active substances in the surfactant-containing products according to the invention is not normally critical. Preferred concentrations depend on the type of surfactant and the particular application. For example, they can be less than 1 wt. % in special bleach products, but greater than 99 wt. % in soaps or washing powder.

Particular combinations and concentrations are preferred in surfactant-containing products according to the invention for particular fields of application. Thus, preferred mixtures according to the invention (detergent formulations) are those in which the proportion of linear alkylbenzenesulfonates is in the range from 7 to 10 wt. % and/or the proportion of fatty alcohol ethoxylates having 12-18 C atoms is in the range from 3 to 6 wt. %, based in each case on the total weight of the mixture. Other preferred mixtures according to the invention (formulations for light-duty detergents, shampoos and shower gels) are those in which the proportion of sodium laurylethersulfate is in the range from 7 to 13 wt. % and/or the proportion of betaine (especially betaine of the acid amide type having the structure shown above) is in the range from 1 to 3 wt. %, based in each case on the total weight of the mixture.

In particular, when the surfactant-containing products are provided for the treatment of hair or textile fibres, another important application technology requirement is their substantivity towards or retention on the substrate, i.e. especially hair or textile fibres. The meaning of substantivity and retention is explained in detail e.g. in EP 1 201 738 A1, cf. sections [0004]-[0005].

The surfactant-containing products containing a mixture according to the invention also exhibit a surprisingly high substantivity towards or retention on hair, wool, cotton and other textile fibres.

The Examples which follow serve to illustrate the invention. Unless indicated otherwise, all the data are by weight.

The Ambrocenide® used in the Examples below was prepared from (-)-alpha-cedrene oxide analogously to Examples 1, 4 and 5 of EP 0 857 723. Ambrocenide® is a commercial product of Symrise GmbH & Co. KG.

EXAMPLE 1

Perfume Oil, Particularly Suitable for Incorporation Into a Shampoo

| | Parts by weight A | Parts by weight B |
|---|---|---|
| Allylamyl glycolate | 4.00 | 4.00 |
| Bergamot oil, furocoumarin-free | 80.00 | 80.00 |
| Calone 1951 (7-methyl-2H-1,5-benzodioxepin-3(4H)-one) | 1.00 | 1.00 |
| Canthoxal (2-methyl-3-(4-methoxyphenyl)propanal) | 2.00 | 2.00 |
| Cassis 345B | 2.00 | 2.00 |
| Cedarleaf oil | 2.00 | 2.00 |
| Cedarwood oil | 5.00 | 5.00 |
| Cypress oil | 7.00 | 7.00 |
| Alpha-damascone | 0.50 | 0.50 |
| Dihydromyrcenol | 150.0 | 150.0 |
| Eugenol | 8.00 | 8.00 |
| Evernyl (methyl 2,4-dihydroxy-3,6-dimethylbenzoate) | 0.50 | 0.50 |
| Fleursandol ((E)-4-(3a,4,5,6,7,7a-hexahydro-3H-4,7-methanoinden-5-yl)-3-methylbut-3-en-2-ol) | 40.00 | 40.00 |
| Florazone (3-(4-ethylphenyl)-2,2-dimethylpropanal) | 5.00 | 5.00 |
| Galaxolid ®, 50% in DEP (4,6,6,7,8,8-hexamethyl-1,3,4,6,7,8-hexahydrocyclopenta[g]benzopyran) | 35.00 | 35.00 |
| Grapefruit base | 3.00 | 3.00 |
| Hedion ® (methyl dihydrojasmonate) | 288.0 | 290.0 |
| Helional ® (2-methyl-3-(3,4-methylenedioxophenyl)propanal) | 60.00 | 60.00 |
| Cis-3-hexenol | 2.00 | 2.00 |
| Iso E Super ® (2,3,8,8-tetramethyl-1,2,3,4,5,6,7,8-octahydro-2-naphthalenyl methyl ketone) | 50.00 | 50.00 |
| Lavender oil Abrialis, natural | 15.00 | 15.00 |
| Lemon oil | 20.00 | 20.00 |
| Vertocitral (2,4-dimethyl-3-cyclohexenecarbaldehyde) | 2.00 | 2.00 |
| Lilial ® (2-methyl-3-(4-tert-butylphenyl)propanal) | 20.00 | 20.00 |
| Linalool | 80.00 | 80.00 |
| Mandarin oil | 20.00 | 20.00 |
| Orange oil, Brazilian | 15.00 | 15.00 |
| Patchouli oil | 10.00 | 10.00 |
| Rosemary oil, Spanish | 5.00 | 5.00 |
| Sage oil, Dalmatian | 3.00 | 3.00 |
| Sandranol ® | 5.00 | 5.00 |
| Tonalid ® (1-(5,6,7,8-tetrahydro-3,5,5,6,8,8-hexamethyl-2-naphthalenyl)ethanone) | 10.00 | 10.00 |
| 3-(4-Methylcyclohex-3-enyl)-butyraldehyde (limonenal) | 47.50 | 47.50 |
| Ambrocenide ®, 10% in DPG | 2.50 | 0.50 |
| TOTAL | 1000.00 | 1000.00 |

Abbreviations: DEP = diethyl phthalate, DPG = dipropylene glycol

Compared with a mixture containing 48 parts by weight of DPG instead of a total of 47.50 parts by weight of limonenal and 0.50 part by weight of Ambrocenide®, 10% in DPG, the above perfume oil containing limonenal and Ambrocenide® had a noticeably more intensely citrus-like, softer and more complex note, the overall composition having a more harmonious effect. Fatty notes were not in evidence.

Compared with a mixture containing 50 parts by weight of DPG instead of a total of 47.50 parts by weight of limonenal and 2.50 parts by weight of Ambrocenide®, 10% in DPG, the above perfume oil containing limonenal and Ambrocenide® had a more citrus-like, warmer, more complex and slightly woody-ambergris note, the overall composition having a more harmonious effect. Fatty notes were not in evidence.

EXAMPLE 2

Shampoo

The perfume oil compositions A and B from Example 1 were separately incorporated, in a dose of 0.4 wt. %, into a shampoo base of the following composition:

| | |
|---|---|
| Sodium laurylethersulfate (e.g. Texapon NSO from Cognis Deutschland GmbH) | 12% |
| Cocamidopropylbetaine (e.g. Dehyton K from Cognis Deutschland GmbH) | 2% |
| Sodium chloride | 1.4% |
| Citric acid | 1.3% |
| Phenoxyethanol, methyl-, ethyl-, butyl- and propylparaben | 0.5% |
| Water | 82.8% |

The pH of the shampoo base was about 6. This is used to prepare 100 ml of a 20 wt. % aqueous shampoo solution (as an Example of a solution according to the invention). Two swatches of hair are washed together for 2 minutes in this shampoo solution and then rinsed for 20 seconds under lukewarm running water. One swatch is packed wet in aluminium foil and the second swatch is dried with a hair dryer. Both swatches are assessed by a panel for their olfactory properties.

EXAMPLE 3

Fabric Softener

The perfume oil compositions A and B from Example 1 were separately incorporated, in a dose of 0.4 wt. %, into a fabric softener base of the following composition:

| | |
|---|---|
| Quaternary ammonium methosulfate (Esterquat), approx. 90% (e.g. Rewoquat WE 18 from Witco Surfactants GmbH) | 5.5% |
| Alkyldimethylbenzylammonium chloride, approx. 50% (e.g. Preventol R50 from Bayer AG) | 0.2% |
| Dye solution, approx. 1% | 0.3% |
| Water | 94.0% |

The pH of the fabric softener base was in the range from 2 to 3. Two cloths are rinsed for 30 minutes at 20° C. with 370 g of a 1% aqueous fabric softener solution prepared from the base (as an Example of a solution according to the invention) in a Linetest machine running the fabric softener programme. The cloths are wrung out and then spun for 20 seconds. One cloth is sealed up wet and one is hung up to dry. Both cloths are then assessed by a panel for their olfactory properties.

EXAMPLE 4

Washing Powder

The perfume oil compositions A and B from Example 1 were separately incorporated, in a dose of 0.3 wt. %, into a washing powder base of the following formulation:

| | |
|---|---|
| Linear Na alkylbenzenesulfonate | 8.8% |
| Ethoxylated C12-18 fatty alcohol (7 EO) | 4.7% |
| Na soap | 3.2% |
| Antifoam | 3.9% |
| (Dow Corning ® 2-4248S Powdered Antifoam, silicone oil on zeolite as carrier) | |
| Zeolite 4A | 28.3% |
| Na carbonate | 11.6% |
| Na salt of an acrylic acid/maleic acid copolymer | 2.4% |
| (Sokalan CP5) | |
| Na silicate | 3.0% |
| Carboxymethyl cellulose | 1.2% |
| Dequest 2066 | 2.8% |
| ([[(phosphonomethyl)imino]bis[(ethylene-nitrilo)bis(methylene)]]tetrakisphosphonic acid, sodium salt) | |
| Optical brightener | 0.2% |
| Na sulfate | 6.5% |
| Protease | 0.4% |
| Sodium perborate tetrahydrate | 22.0% |
| TAED | 1.0% |

Two cloths are washed for 45 minutes at 60° C. with 370 g of a 1% aqueous washing powder liquor prepared from the base (as an Example of a surfactant-containing solution according to the invention, the pH of the washing powder liquor being well in the basic range) in a Linetest machine running the main washing cycle. The cloths are first rinsed for 5 minutes with cold water, wrung out and then spun for 20 seconds. One cloth is sealed up wet and one is hung up to dry. Both cloths are then assessed by a panel for their olfactory properties.

Further Embodiments

In a first embodiment, the present invention is a mixture comprising or consisting or consisting essentially of 3-(4-methylcyclohex-3-enyl)butyraldehyde (limonenal) and (4aR,5R,7aS,9R)-octahydro-2,2,5,8,8,9a-hexamethyl-4H-4a,9-methanoazuleno(5,6-d)-1,3-dioxole (Ambrocenide®), wherein the weight ratio of limonenal to Ambrocenide® is in the range from 150:1 to 2500:1. A second embodiment is a mixture according to the first embodiment wherein the weight ratio of limonenal to Ambrocenide® is in the range from 600:1 to 2500:1, preferably in the range from 800:1 to 2500:1. A third embodiment is a mixture according to one of the first through second embodiments, further comprising one or more diluents or solvents selected from the group consisting of ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), benzyl benzoate (BB) and benzyl acetate.

A fourth embodiment is a mixture according to the third embodiment wherein the weight ratio of Ambrocenide® to the total amount of said diluent(s) or solvent(s) is in the range from 1:99 to 1:1, preferably in the range from 5:95 to 1:3. A fifth embodiment is a mixture according to one of the first through fourth embodiments, wherein the mixture is a fragrance mixture comprising, apart from limonenal and Ambrocenide®, at least an equal proportion by weight of one or more other fragrances. A sixth embodiment is the use of Ambrocenide® for masking the fatty olfactory note of limonenal.

A seventh embodiment is a method of masking the fatty olfactory note of limonenal, comprising mixing of limonenal with an amount of Ambrocenide® that partially or completely masks the fatty olfactory note of limonenal. An eighth embodiment is a method according to the seventh embodiment wherein the amount of Ambrocenide® used is chosen so that the woody and/or ambergris note of the Ambrocenide® does not dominate over the fresh and/or citrus note of the limonenal.

A ninth embodiment is the method according to the seventh or eighth embodiments wherein the weight ratio of limonenal to Ambrocenide® in the mixture is adjusted to a value in the range from 150:1 to 2500:1, preferably in the range from 600:1 to 2500:1.

A tenth embodiment is the use of a mixture according to one of the second through fifth embodiments as a fragrance with a fresh, citrus-like note.

The invention claimed is:

1. A mixture comprising 3-(4-methylcyclohex-3-enyl)butyraldehyde (limonenal) and (4aR,5R,7aS,9R)-octahydro-2,2,5,8,8,9a-hexamethyl-4H-4a,9-methanoazuleno(5,6-d)-1,3-dioxole, wherein the weight ratio of limonenal to (4aR,5R,7aS,9R)-octahydro-2,2,5,8,8,9a-hexamethyl-4H-4a,9-methanoazuleno(5,6-d)-1,3-dioxole is in the range from 150:1 to 2500:1.

2. The mixture of claim 1 consisting essentially of 3-(4-methylcyclohex-3-enyl)-butyraldehyde (limonenal) and (4aR,5R7aS,9R)-octahydro-2,2,5,8,8,9a-hexamethyl-4H-4a,3-methanoazuleno(5,6-d)-1,3-dioxole, wherein the weight ratio of limonenal to (4aR,5R,7aS,9R)-octahydro-2,2,5,8,8,9a-hexamethyl-4H-4a,9-methanoazuleno(5,6-d)-1,3-dioxole is in the range from 150:1 to 2500:1.

3. The mixture of claim 1 consisting of 3-(4-methylcyclohex-3-enyl)butyraldehyde (limonenal) and (4aR,5R,7aS,9R)-octahydro-2,2,5,8,8,9a-hexamethyl-4H-4a,9-methanoazuleno(5,6-d)-1,3-dioxole, wherein the weight ratio of limonenal to (4aR,5R,7aS,9R)-octahydro-2,2,5,8,8,9a-hexamethyl-4H-4a,9-methanoazuleno(5,6-d)-1,3-dioxole is in the range from 150:1 to 2500:1.

4. The mixture of claim 1, wherein the weight ratio of limonenal to (4aR,5R,7aS,9R)-octahydro-2,2,5,8,8,9a-hexamethyl-4H-4a,9-methanoazuleno(5,6-d)-1,3-dioxole is in the range from 600:1 to 2500:1.

5. The mixture of claim 1, wherein the weight ratio of limonenal to (4aR,5R,7aS,9R)-octahydro-2,2,5,8,8,9a-hexamethyl-4H-4a,9-methanoazuleno(5,6-d)-1,3-dioxole is in the range from 800:1 to 2500:1.

6. The mixture of claim 2, wherein the weight ratio of limonenal to (4aR,5R,7aS,9R)-octahydro-2,2,5,8,8,9a-hexamethyl-4H-4a,9-methanoazuleno(5,6-d)-1,3-dioxole is in the range from 800:1 to 2500:1.

7. The mixture according to claim 1, further comprising one or more diluents or solvents selected from the group consisting of ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), benzyl benzoate (BB) and benzyl acetate.

8. The mixture of claim 7, wherein the weight ratio of (4aR,5R,7aS,9R)-octahydro-2,2,5,8,8,9a-hexamethyl-4H-4a,9-methanoazuleno(5,6-d)-1,3-dioxole to the total amount of said diluent(s) or solvent(s) is in the range from 1:99 to 1:1.

9. A fragrance mixture comprising the mixture of claim 1, and further comprising at least an equal proportion by weight of one or more other fragrances.

10. A method of masking the fatty olfactory note of limonenal comprising: mixing limonenal with an amount of (4aR,5R,7aS,9R)-octahydro-2,2,5,8,8,9a-hexamethyl-4H-4a,9-methanoazuleno(5,6-d)-1,3-dioxole the partially or completely masks the fatty olfactory note of limonenal, wherein the weight ratio of limonenal to (4aR,5R,7aS,9R)-octahydro-2,2,5,8,8,9a-hexamethyl-4H-4a,9-methanoazuleno(5,6-d)-1,3-dioxole in the mixture is in the range from 150:1 to 2500:1.

11. The method of claim 10, wherein the weight ratio of limonenal to (4aR,5R,7aS,9R)-octahydro-2,2,5,8,8,9a-hexamethyl-4H-4a,9-methanoazuleno(5,6-d)-1,3-dioxole in the mixture is in the range from 600:1 to 2500:1.

12. A method of preparing a fragrance composition comprising the steps of mixing together 3-(4-methylcyclohex-3-enyl)butyraldehyde (limonenal); (4aR,5R,7aS,9R)-octahydro-2,2,5,8,8,9a-hexamethyl-4H-4a,9-methanoazuleno(5,6-d)-1,3-dioxole (4aR,5R,7aS,9R)-octahydro-2,2,5,8,8,9a-hexamethyl-4H-4a,9-methanoazuleno(5,6-d)-1,3-dioxole, and one or more other fragrances, wherein the weight ratio of limonenal to (4aR,5R,7aS,9R)-octahydro-2,2,5,8,8,9a-hexamethyl-4H-4a,9-methanoazuleno(5,6-d)-1,3-dioxole is in the range from 150:1 to 2500:1.

13. The method of claim 12, wherein the fragrance composition has a fresh, citrus-like note.

* * * * *